US006479454B1

(12) United States Patent
Smith et al.

(10) Patent No.: US 6,479,454 B1
(45) Date of Patent: Nov. 12, 2002

(54) ANTIMICROBIAL COMPOSITIONS AND METHODS CONTAINING HYDROGEN PEROXIDE AND OCTYL AMINE OXIDE

(75) Inventors: Kim R. Smith, Woodbury, MN (US); Robert D. P. Hei, Bladwin, WI (US)

(73) Assignee: Ecolab Inc., St. Paul, MN (US)

(*) Notice: Subject to any disclaimer, the term of this patent is extended or adjusted under 35 U.S.C. 154(b) by 44 days.

(21) Appl. No.: 09/680,566

(22) Filed: Oct. 5, 2000

(51) Int. Cl.[7] .................... C11D 1/75; C11D 3/395
(52) U.S. Cl. ............... 510/503; 510/218; 510/234; 510/235; 510/237; 510/238; 510/247; 510/276; 510/302; 510/309; 510/310; 510/362; 510/367; 510/372; 510/375; 510/378
(58) Field of Search ................... 510/218, 234, 510/235, 237, 238, 247, 276, 302, 309, 310, 362, 367, 372, 375, 378, 503

(56) References Cited

U.S. PATENT DOCUMENTS

| | | |
|---|---|---|
| 2,512,640 A | 6/1950 | Greenspan et al. |
| 3,122,417 A | 2/1964 | Blaser et al. |
| 3,248,281 A | 4/1966 | Goodenough |
| 3,350,265 A | 10/1967 | Rubinstein et al. |
| 3,514,278 A | 5/1970 | Brink |
| 3,895,116 A | 7/1975 | Herting et al. |
| 3,996,386 A | 12/1976 | Malkki et al. |
| 4,041,149 A | 8/1977 | Gaffar et al. |
| 4,051,058 A | 9/1977 | Böwing et al. |
| 4,051,059 A | 9/1977 | Böwing et al. |
| 4,129,517 A | 12/1978 | Eggensperger et al. |
| 4,191,660 A | 3/1980 | Schreiber et al. |
| 4,244,844 A | 1/1981 | Hutchins et al. |
| 4,370,199 A | 1/1983 | Orndorff |
| 4,404,040 A | 9/1983 | Wang |
| 4,477,438 A | 10/1984 | Willcockson et al. |
| 4,478,683 A | 10/1984 | Orndorff |
| 4,501,681 A | 2/1985 | Groult et al. |
| 4,529,534 A | 7/1985 | Richardson |
| 4,557,898 A | 12/1985 | Greene et al. |
| 4,592,488 A | 6/1986 | Simon et al. |
| 4,613,452 A | 9/1986 | Sanderson |
| 4,655,781 A | 4/1987 | Hsieh et al. |
| 4,666,622 A | 5/1987 | Martin et al. ............ 252/99 |
| 4,715,980 A | 12/1987 | Lopes et al. |
| 4,738,840 A | 4/1988 | Simon et al. |
| 4,802,994 A | 2/1989 | Mouché et al. |
| 4,865,752 A | 9/1989 | Jacobs |
| 4,900,721 A | 2/1990 | Bansemir et al. |
| 4,906,617 A | 3/1990 | Jacquet et al. |
| 4,908,306 A | 3/1990 | Lorincz |
| 4,917,815 A | 4/1990 | Beilfuss et al. |
| 4,923,677 A | 5/1990 | Simon et al. |
| 4,937,066 A | 6/1990 | Vlock |
| 4,943,414 A | 7/1990 | Jacobs et al. |
| 4,945,110 A | 7/1990 | Brokken et al. |
| 4,996,062 A | 2/1991 | Lehtonen et al. |
| 4,997,571 A | 3/1991 | Roensch et al. |
| 4,997,625 A | 3/1991 | Simon et al. |
| 5,004,760 A | 4/1991 | Patton et al. |
| 5,010,109 A | 4/1991 | Inoi |
| 5,015,408 A | 5/1991 | Reuss |
| 5,043,176 A | 8/1991 | Bycroft et al. |
| 5,069,286 A | 12/1991 | Roensch et al. |
| 5,078,896 A | 1/1992 | Rorig et al. ............. 252/102 |
| 5,084,239 A | 1/1992 | Moulton et al. |
| 5,093,140 A | 3/1992 | Watanabe |
| 5,114,178 A | 5/1992 | Baxter |
| 5,114,718 A | 5/1992 | Damani |
| 5,122,538 A | 6/1992 | Lokkesmoe et al. |
| 5,129,824 A | 7/1992 | Keller |
| 5,130,124 A | 7/1992 | Merianos et al. |
| 5,139,788 A | 8/1992 | Schmidt |
| 5,176,899 A | 1/1993 | Montgomery |
| 5,200,189 A | 4/1993 | Oakes et al. |
| 5,208,057 A | 5/1993 | Greenley et al. |
| 5,234,703 A | 8/1993 | Guthery |
| 5,234,719 A | 8/1993 | Richter et al. |
| 5,268,003 A | 12/1993 | Coope et al. |
| 5,292,447 A | 3/1994 | Venturello et al. |
| 5,314,687 A | 5/1994 | Oakes et al. |
| 5,336,500 A | 8/1994 | Richter et al. |
| 5,364,650 A | 11/1994 | Guthery |
| 5,391,324 A | 2/1995 | Reinhardt et al. |
| 5,409,713 A | 4/1995 | Lokkesmoe et al. |

(List continued on next page.)

FOREIGN PATENT DOCUMENTS

| | | |
|---|---|---|
| CA | 2181416 | 7/1996 |
| DE | 1 494109 | 12/1973 |
| DE | 35 43 500 A1 | 6/1987 |
| DE | 39 06 044 A1 | 8/1990 |

(List continued on next page.)

OTHER PUBLICATIONS

Nov. 12, 1998, Search Report for the use of amine oxides with hydrogen peroxide in bleaching, sanitizing, disinfectant or hard surface cleaners.

Bell, K. et al., "Reduction of foodborne micro–organisms on beef carcass tissue using acetic acid, sodium bicarbonate, and hydrogen peroxide spray washes", *Food Microbiology*, vol. 14, pp. 439–448 (1997).

(List continued on next page.)

*Primary Examiner*—Charles Boyer
(74) *Attorney, Agent, or Firm*—Merchant & Gould P.C.

(57) ABSTRACT

A peroxygen antimicrobial composition is provided comprising an amine oxide and peroxygen compound. The combination of the two components produces an effective antimicrobial composition, providing a more potent biocide than can be obtained by using these compounds separately. Other components can be added to the composition such as peracetic acid, acetic acid, hydrotrope coupling agents, etc. The composition can be used to sanitize various surfaces such as hard surfaces found in food processing, food service and health care industries as well as to sanitize the surfaces of food and in the treatment of water.

16 Claims, No Drawings

U.S. PATENT DOCUMENTS

| | | | |
|---|---|---|---|
| 5,419,908 A | | 5/1995 | Richter et al. |
| 5,435,808 A | | 7/1995 | Holzhauer et al. |
| 5,436,008 A | | 7/1995 | Richter et al. |
| 5,437,868 A | | 8/1995 | Oakes et al. |
| 5,489,434 A | | 2/1996 | Oakes et al. |
| 5,494,588 A | | 2/1996 | LaZonby |
| 5,508,046 A | | 4/1996 | Cosentino et al. |
| 5,512,309 A | | 4/1996 | Bender et al. |
| 5,578,134 A | * | 11/1996 | Lentsch et al. ............ 134/3 |
| 5,591,706 A | | 1/1997 | Ploumen |
| 5,595,967 A | | 1/1997 | Miracle et al. |
| 5,597,790 A | | 1/1997 | Thoen |
| 5,616,335 A | | 4/1997 | Nicolle et al. |
| 5,616,616 A | | 4/1997 | Hall et al. |
| 5,632,676 A | | 5/1997 | Kurschner et al. |
| 5,641,530 A | | 6/1997 | Chen |
| 5,656,302 A | | 8/1997 | Cosentino et al. |
| 5,658,467 A | | 8/1997 | LaZonby et al. |
| 5,674,538 A | | 10/1997 | Lokkesmoe et al. |
| 5,674,828 A | | 10/1997 | Knowlton et al. ......... 510/372 |
| 5,683,724 A | | 11/1997 | Hei et al. |
| 5,712,239 A | | 1/1998 | Knowlton et al. |
| 5,718,910 A | | 2/1998 | Oakes et al. |
| 5,756,139 A | | 5/1998 | Harvey et al. |
| 5,785,867 A | | 7/1998 | LaZonby et al. |
| 5,840,343 A | | 11/1998 | Hall et al. |
| 5,851,483 A | | 12/1998 | Nicolle et al. |
| 5,891,392 A | | 4/1999 | Moticello et al. |
| 5,900,256 A | | 5/1999 | Scoville, Jr. et al. |
| 5,902,619 A | | 5/1999 | Rubow et al. |
| 5,968,539 A | | 10/1999 | Beerse et al. |
| 5,989,611 A | | 11/1999 | Stemmler, Jr. et al. |
| 5,998,358 A | | 12/1999 | Herdt et al. ............ 510/506 |
| 6,010,729 A | | 1/2000 | Gutzmann et al. |
| 6,024,986 A | | 2/2000 | Hei |
| 6,033,705 A | | 3/2000 | Isaacs |
| 6,049,002 A | | 4/2000 | Mattila et al. |
| 6,080,712 A | * | 6/2000 | Revell et al. ............ 510/372 |
| 6,096,226 A | | 8/2000 | Fuchs et al. |
| 6,096,266 A | | 8/2000 | Duroselle |
| 6,096,348 A | | 8/2000 | Miner et al. |
| 6,096,349 A | * | 8/2000 | Petri et al. ............. 424/616 |
| 6,168,808 B1 | * | 1/2001 | Godin et al. ............ 424/616 |

FOREIGN PATENT DOCUMENTS

| | | |
|---|---|---|
| DE | 197 51 391 A1 | 7/1998 |
| EP | 0 195 619 A2 | 9/1986 |
| EP | 0 233 731 A2 | 8/1987 |
| EP | 0 404 293 A2 | 3/1990 |
| EP | 0 461 700 A1 | 12/1991 |
| EP | 0 569 066 A1 | 11/1993 |
| EP | 0 667 392 A2 | 2/1995 |
| EP | 0 779 357 A1 | 12/1995 |
| EP | 0 805 198 A1 | 7/1996 |
| EP | 0 843 001 A1 | 11/1996 |
| EP | 805198 * | 11/1997 |
| EP | 0 985 349 A2 | 3/2000 |
| FR | 2 321 301 A | 3/1977 |
| FR | 2 324 626 A | 4/1977 |
| GB | 2 255 507 A | 5/1991 |
| LU | 78 568 A | 4/1978 |
| RU | 2102447 | 1/1998 |
| WO | WO 93/01716 | 2/1993 |
| WO | WO 94/21122 | 9/1994 |
| WO | WO 94/23575 | 10/1994 |
| WO | WO 95/34537 | 12/1995 |
| WO | WO 96/30474 | 3/1996 |
| WO | WO 98/28267 | 7/1998 |
| WO | WO 99/51095 | 10/1999 |

OTHER PUBLICATIONS

Eggensperger, H., "Disinfectants Based on Peracid–Splitting Compounds", *Zbl. Bakt. Hyg.,* I. Abt. Orig. B 168, pp. 517–524 (1979).

Lion C. et al., "New decontaminants. Reaction of peroxyacid esters with toxic insecticides", *Bull. Soc. Chim. Belg.,* vol. 100, No. 7, pp. 555–559 (1991).

Merka, V. et al., "Disinfectant properties of some peroxide compounds.", Abstract No. 67542e, *Chemical Abstracts,* vol. 67 (1967).

Mulder, R.W.A.W. et al., "Research Note: Salmonella Decontamination of Broiler Carcasses with Lactic Acid, L–Cysteine, and Hdrogen Peroxide", *Poultry Science,* vol. 66, pp. 1555–1557 (1987).

Parker, W. et al., "Peroxides. II. Preparation, Characterization and Polarographic Behavior of Longchaing Aliphatic Peracids", *Synthesis and Properties of LongChain Aliphatic Peracids,* vol. 77, pp. 4037–4041 (Aug. 5, 1955).

Parker, W. et al., "Peroxides. IV. Aliphatic Diperacids", *Aliphatic Diperacids,* vol. 79, pp. 1929–1931 (Apr. 20, 1957).

Towle, G. et al., "Industrial Gums polysaccharides and Their Derivatives", Second Edition, Ch. XIX, "Pectin", pp. 429–444 (year unknown).

Armak Chemicals, "NEO–FAT Fatty Acids", *Akzo Chemicals Inc.,* Bulletin No. 86–17 (1986).

Computer search results—Level 1—5 patents (Mar. 1994).

Computer search results from Ecolab Information Center (Jun. 1998).

"Emery® Fatty and Dibasic Acids Specifications and Characteristics", *Emery Industries,* Bulletin 145, (Oct. 1983).

Pfizer Chemical Division, "Pfizer Flocon® Biopolymers for Industrial Uses (xanthan broths)", Data Sheet 679, pp. 1–4 (year unknown).

"Indirect food additives: adjuvants, production aids, and sanitizers", *Fed. Regist.,* vol. 61, No. 108, pp. 28051–28053 (Jun. 4, 1996) (abstract only).

Search Result from Database WPI and Database INPADOC.

Copy of International Search Report dated Jan. 30, 2002 (10 pages).

* cited by examiner

ANTIMICROBIAL COMPOSITIONS AND METHODS CONTAINING HYDROGEN PEROXIDE AND OCTYL AMINE OXIDE

FIELD OF THE INVENTION

The disclosure relates generally to antimicrobial or biocidal compositions and more particularly to peroxygen antimicrobial compositions for reducing microbe populations on food surfaces, hard surfaces found in food processing, food services and health care industries, dish sanitizing and water treatment.

BACKGROUND OF THE INVENTION

Numerous classes of chemical compounds exhibit varying degrees of antimicrobial or biocidal activity. Antimicrobial compositions are needed, among other things, to clean and disinfect food surfaces such as fruits and vegetables and to clean and disinfect hard-surfaces in the health care industry, food and beverage industries and household arena.

Prior art hard surface cleaner compositions often relate to acid cleaners containing formulated detergent compositions. Casey, U.S. Pat. No. 4,587,030, discloses a composition formulated to remove soap scum and hardness components using an aqueous base containing a surfactant system, and formulations of an amine oxide and cosolvent. Reihm et al., U.S. Pat. No. 4,699,728, discloses a fiberglass cleaner composition containing an organophosphonic acid/acrylic acid sequestrant in combination with a betaine surfactant. Sanitizing compositions have also been formulated in the past to combat microbial growth on hard surfaces. For example, Wang, U.S. Pat. No. 4,404,040, teaches a short chain fatty acid sanitizing composition comprising an aliphatic short chain fatty acid, a hydrotrope solubilizer capable of solubilizing the fatty acid in both the concentrate and use solution.

Compositions having cleaning and sanitizing effectiveness have been disclosed which include one or more surfactants and one or more antimicrobial agents, where the surfactant is effective at removal of soils, especially soils that contain fats, and the antimicrobial agents such as ethylene oxide, strong acids and compositions of aldehydes are known to have varying degrees of biocidal activity. Limitations exist for many of these cleaning compositions in that the antimicrobial agents exhibit toxic, corrosive and irritant properties that limit the compositions usefulness, especially in relation to the food and beverage industries.

Other less corrosive and less toxic antimicrobial agents are known for use in these compositions, for example, peroxy-containing compositions are disclosed in Bowing et al., U.S. Pat. No. 4,051,059, where the composition contains peracetic acid, acetic acid or mixtures of peracetic and acetic acid, hydrogen peroxide, anionic surface active compounds such as sulfonates and sulfates, and water. Additionally, Knowlton et al., U.S. Pat. No. 5,674,828, discloses a liquid peracid bleach comprising a surfactant, a defined peroxyacid and a complex amine oxide.

Peracetic acid alone is known to be a good microbiocidal agent at fairly high concentrations. Similarly, peroxyfatty acids have been shown to be biocidal at fairly high concentrations, such as in the composition disclosed in European Patent Application No. 233, 731. However, antimicrobial compositions having low use concentrations of the antimicrobial agent which effectively kill microbes and provide a satisfactory ability to remove soil are particularly desirable. Low concentrations of the antimicrobial agent minimize use cost, surface corrosion, odor, carryover of biocide into foods and potential toxic effects to the user. Therefore, a continuing need exists to provide an antimicrobial composition for use in cleaning and disinfecting food surfaces, and in cleaning and disinfecting hard surfaces in the food and beverage and health care industries. Against this backdrop the present invention has been developed.

SUMMARY OF THE INVENTION

Aspects of the present invention are directed at compositions that include effective microbiocidal amounts of an amine oxide and peroxygen compound. The compositions can be used to reduce microbe populations on hard surfaces, food, dishware and in water.

One aspect of the present invention is a composition including a peroxygen compound combined with an amine oxide. The composition can be in the form of a concentrate or can be diluted to an end use composition. Typically, the concentrate is 0.1 to 40 wt. % peroxygen compound and 0.1 to 40 wt. % amine oxide. Other components may be added such as carboxylic acids, surfactant hydrotrope coupling agents or solubilizers, esters, chelating agents, etc.

Another aspect of the present invention is a composition including a peroxygen compound mixed with peracetic acid and an amine oxide. As above, the composition can be in the form of a concentrate or can be diluted to an end use composition. Typically, the concentrate is 0.1 to 40 wt. % of a mixture of the peroxygen compound and peracetic acid and 0.1 to 40-wt. % amine oxide. Other components may be added such as carboxylic acids, surfactant hydrotrope coupling agents or solubilizers, esters, chelating agents, etc.

The concentrate of the composition may be diluted in a major proportion of an aqueous fluid to form an antimicrobial use solution. The use solution may have a peroxygen compound of 10 to 10,000 ppm in combination with an amine oxide of 10 to 10,000 ppm. As with the concentrate the peroxygen compound may be in a mixture with peracetic acid to obtain the use solution concentrations. Other components may be added such as carboxylic acids, surfactant hydrotrope coupling agents or solubilizers, esters, chelating agents, etc.

Another aspect of the present invention is a process of reducing microbial populations on contaminated surfaces including the steps of selecting an antimicrobial composition typically having 0.1 to 40 wt. % of a peroxygen compound and 0.1 to 40 wt. % of an amine oxide, and contacting the contaminated surface with the composition. The selected composition may include a mixture of 0.1 to 40 wt. % peroxygen compound and peracetic acid and 0.1 to 40 wt. % of an amine oxide. Other components may be added such as carboxylic acids, surfactant hydrotrope coupling agents or solubilizers, esters, chelating agents, etc.

One aspect of the present invention is the novel, antimicrobial concentrate composition which is capable of being diluted with a major proportion of water or other aqueous based liquid to form a use solution. Another aspect of the present invention is an aqueous antimicrobial use solution which is particularly suited for "in-place" cleaning applications. Another aspect of the present invention is a process of employing the composition of the present invention in the reduction of microbial populations on various contaminated surfaces. Another aspect of the present invention is a method of employing the composition of the present invention in the reduction of microbial populations on various process facilities or equipment as well as other surfaces.

DETAILED DESCRIPTION OF THE INVENTION

The present invention resides in antimicrobial compositions including an effective microbiocidal amount of an amine oxide and peroxygen compound. The combination of the amine oxide and the peroxygen compound advantageously provides a synergistic effect, producing a much more potent biocide than can be obtained by using these compositions separately. The antimicrobial composition can be used effectively to reduce the microbial population of hard surfaces such as those in facilities and equipment used in the food and beverage industries. Additionally, the present composition can be used to effectively reduce the microbial population of food, of dishware, and to treat water.

Definitions

The term "sanitizing" is used in the present disclosure to mean an agent that reduces the number of microbes. The term disinfect means a 99.9% reduction in microbes. Sterilize means the elimination of substantially all microbes from the target.

The term Minimal Bactericidal Concentration is used in the present invention to mean a 5 log reduction in microbe count.

The term microbe is used in the present invention to mean a microorganism such as a bacterium, spore, fungi, virus, mycobacteria, etc.

The term contaminated surface is used in the present invention to mean a surface, including a surface of food, soiled with a microbe.

The term weight ratio is used in the present invention to be equal to the weight in grams of a solute per 100 grams of a solution.

The term aqueous liquid is used in the present invention to mean a solution where the solvent is water or other miscible solution like alcohol, etc.

The term chelating agent is used in the present invention to mean a compound having atoms which form a coordinate bond(s) with metals while in solution.

The term solution is used in the present invention to mean any mixture of two or more substances.

Peroxygen Compounds

A preferred embodiment of the present invention is based upon the fact that when an amine oxide is combined with a peroxygen compound, a synergistic effect is produced and greatly enhanced antimicrobial activity is exhibited when compared to the amine oxide alone or the peroxygen compound alone. The present blend of a amine oxide and a peroxygen compound can effectively kill microorganisms (e.g., a 3 $\log_{10}$ reduction in 30 seconds) from a concentration level of 10–10,000 ppm of a peroxygen compound, such as hydrogen peroxide, in combination with 10–10,000 ppm of an amine oxide.

The term peroxygen compound refers to any compound having a chemical formula including a —O—O— structure. A variety of peroxygen compounds may be employed in the present invention, including both organic and inorganic peroxides. One possible class of peroxygen compounds are peroxyacids such as peroxyfatty acids, monoperoxy or diperoxydicarboxylic acids, and peroxyaromatic acids. The peroxyacids employed in the present invention may be structurally represented as follows: $R_1$—$CO_3H$ wherein $R_1$ is a hydrocarbon moiety having from about 1–18 carbon atoms. $R_1$ may have substituents in or at the end of the chain, e.g., —OH, $CO_2H$, or heteroatoms (e.g., —O— as in alkylether carboxylic acids), as long as the antimicrobial properties of the compositions are not significantly affected. It should be understood that "$R_1$" chain substituents or heteroatoms may change the overall acidity (i.e., pKa) of the acids herein described. Such modification is within the contemplation of the present invention provided the advantageous antimicrobial performance is maintained. Furthermore, $R_1$ may be saturated, unsaturated, linear, branched, cyclic or aromatic. Preferred hydrocarbon moieties for $R_1$ include linear, saturated, hydrocarbon and aliphatic moieties. Two preferred peroxyacids for use in the present invention are peracetic acid and peroctanoic acid.

Examples of suitable carboxylic fatty acids which can be reacted with hydrogen peroxide to form peroxyfatty acid include such saturated fatty acids as hexonoic, enanthic, caprylic, pelargonic, capric, undecylic, lauric, trideclic, myristic, palmitic and stearic. These acids may be derived from either natural or synthetic sources. Natural sources include animal and vegetable fats and oils which should be fully hydrogenated. Synthetic acids can be produced by the oxidation of petroleum wax and other routes known to those skilled in the art. Examples of suitable short chain carboxylic acids include: acetic, propionic and butyric acids.

Other suitable peroxyacids are derived from the oxidation of dicarboxylic acids or aromatic acids. Suitable dicarboxylic acids are succinic, glutamic and adipic acids. An example of a suitable aromatic acid is benzoic acid. The mono-ester peracids of the dicarboxylic acids are also useful. Examples include the mono methyl, ethyl, propyl, isoproply or butyl esters of adipic, succinic, glutamic, or mixtures thereof.

The peroxygen compounds used in the present invention can also be produced in a simple manner by mixing a hydrogen peroxide ($H_2O_2$) solution with the desired amount of target acid.

Another peroxygen compound that can be used in the present invention is hydrogen peroxide. Hydrogen peroxide can be used in any form including, for example, anhydrous liquid or aqueous solution.

Finally, ozone, peresters, persulfate salts and perborate salts can also be suitable peroxygen compounds for use in the present invention.

Amine Oxide

Amine oxides are a class of organic compounds having a general formula of

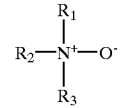

wherein $R_1$, $R_2$, and $R_3$ are independently selected from saturated or unsaturated and straight or branched alkyl groups having from 1–24 carbons and aromatic groups, etc. and which may optionally contain O or N as a heteroatom or polyalkoxy groups. A variety of amine oxides may be employed in the composition of the present invention. Examples of amine oxides include, but are not limited to: alkyldimethylamine oxide, dialkylmethylamine oxide, alkyldialkoxylamine oxide, dialkylalkoxyamine oxide, dialkyletheramine oxide and dialkoxyetheramine oxide. Preferably, $R_1$ is an alkyl group having 4–18 carbons and $R_2$ and $R_3$ are alkyl groups having 1–18 carbons. Most preferably, $R_1$ is an alkyl group having 6–10 carbons and $R_2$ and $R_3$ are alkyl groups having 1–2 carbons.

Other Components

Various optional components may be added to further enhance the present invention's antimicrobial activity. The composition of the invention can include carboxylic acids having the general formula RCOOH to modify pH and to increase the compositions biocidal potential. Any carboxylic acid may be used provided it does not react with the other components of the composition or negatively affect the antimicrobial properties of the composition. An example carboxylic acid includes carboxylic acids wherein the R is a linear, branched, cyclic or aromatic group in nature. An example suitable for use in the present invention includes: aromatic carboxylic acids such as benzoic acid, salicylic acid or phenylacetic acid, alkyl carboxylic acids like acid acetic, formic acid, butyric acid, heptanoic acid, octanoic acid, decanoic acid, propanoic acid or mixtures thereof. Dicarboxylic acids may also be used in the present invention, suitable examples include oxalic acid or malonic acid.

When used, a carboxylic acid can comprise about 1% to 80 wt. %, typically about 5% to 60 wt. %, and preferably about 10% to 40 wt. % of the concentrate composition.

Additionally, the composition of the invention can contain a surfactant hydrotrope coupling agent or solubilizer that permits further blending of short chain perfatty acids in aqueous liquids. Any hydrotrope coupling agent may be used provided it does not react with the other components of the composition or negatively affect the antimicrobial properties of the composition. Representative classes of hydrotropic coupling agents include anionic surfactants such as alkyl sulfates and alkane sulfonates, linear alkyl benzene or naphthalene sulfonates, secondary alkane sulfonates, alkyl ether sulfates and sulfonates, alkyl phosphates or phosphonates dialkyl sulfosuccinic acid esters, and sugar esters.

The hydrotrope coupling agent can comprise about 0.1% to 30 wt. %, preferably about 1 to 15 wt. %, and most preferably about 2 to 15 wt. % of the concentrate composition.

Compounds to suppress foam such as mono, di and trialkyl phosphate esters may be added to the composition. Such phosphate esters would generally be produced from aliphatic linear alcohols, there being from about 6–20 carbon atoms in the aliphatic portions of the alkyl phosphate esters.

Chelating agents can also be added to the composition of the invention to enhance biocidal activity, cleaning performance and stability of the peroxygen compounds. For example, 1-hydroxyethylidene -1,1-diphosphonic acid commercially available from Monsanto Company under the designation "DEQUEST" can be effective. Chelating agents can be added to the present composition to control or sequester hardness ions such as calcium and magnesium. In this manner both detergency and sanitation capability can be enhanced.

Other materials which are sufficiently stable at low pH contemplated by the present composition may be added to the composition to impart desirable qualities depending upon the intended ultimate use. Compounds can be added to the composition to change its color or odor, to adjust its viscosity, to enhance its thermal stability or to provide other qualities which tend to make it more marketable.

Concentrate and Use Compositions

The present invention contemplates a concentrate composition which is diluted to a use solution prior to its utilization as a sanitizer or disinfectant. Primarily for reasons of economics, the concentrate would normally be marketed and the end user would dilute the concentrate with water or other aqueous based material to a use solution. One preferred antimicrobial concentrate composition comprises about 0.1% to 60 wt. %, preferably 0.1% to 40 wt. %, and more preferably 0.1% to 20 wt % of peroxygen compound and about 0.1% to 60 wt. %, preferably 0.1% to 40 wt. %, and more preferably 0.1% to 20 wt % of an amine oxide. Another preferred antimicrobial concentrate composition comprises a 0.1% to 60 wt. %, preferably 0.1% to 40 wt. % and more preferably 0.1 to 20 wt % mixture of peroxygen compound and peracetic acid and about 0.1% to 60 wt. %, preferably 0.1% to 40 wt. %, and more preferably 0.1 to 20 wt % of an amine oxide. Other constituents may optionally be employed in the composition such as acetic acid. It should also be noted that a preferred peroxygen compound may be hydrogen peroxide.

The level of active components in the concentrate composition is dependent upon the intended dilution factor and desired acidity of the use solution. The concentrate composition above is diluted with water or other aqueous solution to provide the use solution. A dilution of a 2 ml mixture of 5% peroxygen compound/5% amine oxide to 1 liter of water gives a 0.02% final concentration of the composition. Other substances besides water can be used to dilute the concentrate, as long as the concentrate performs with its intended purpose. Other dilutions can be employed as use conditions are changed. For example, higher use dilution can be employed if elevated use temperature (greater than 20° C.) or extended time exposure (greater than 30 seconds) are employed. The concentrate can be diluted with a major proportion of water and used for purposes of microbial population reduction.

An aqueous antimicrobial use solution comprises at least about 10 parts per million (ppm) to 10,000 ppm, preferably about 100 ppm to 5,000 ppm, and more preferably about 500 ppm to 2,000 ppm of a peroxygen compound, preferably hydrogen peroxide, and at least 10 ppm to 10,000 ppm, preferably about 100 ppm to 5,000 ppm, and more preferably about 500 ppm to 2,000 ppm of an amine oxide. Alternatively, the antimicrobial use solution comprises at least about 10 part per million (ppm) to 10,000 ppm, preferably about 100 ppm to 5,000 ppm, and more preferably about 500 ppm to 2,000 ppm of a mixture of a peroxygen compound, preferably hydrogen peroxide, and peracetic acid and at least 10 ppm to 10,000 ppm, preferably about 100 ppm to 5,000 ppm, and more preferably about 500 ppm to 2,000 ppm of an amine oxide.

The weight ratio of amine oxide to peroxygen compound ranges from 5.0:1.0 to 1.0:5.0, typically 3.0:1.0 to 1.0:3.0, preferably 1.0:1.0 to 1.0: 1.5, and more preferably 1.0:1.2 to 1.0:1.3 amine oxide:peroxygen compound. Alternatively, the weight ratio of amine oxide to a peroxygen compound, peracetic acid mixture ranges from 5.0:1.0 to 1.0:5.0, preferably 1.0:1.0 to 5.0:1.0 amine oxide:(hydrogen peroxide/peracetic acid). In the case of the hydrogen peroxide/peracetic acid mixture, a weight ratio can be 5.0:1.0 to 1.0:5.0, typically 3.0:1.0 to 1.0:3.0, preferably 1.0:0.8 to 1.0:1.3 hydrogen peroxide:peracetic acid. Finally, if acetic acid is used in the final use solution, it should be at a weight ratio in comparison to peracetic acid of 1.0:0.8 to 1.0:3.0 peracetic acid:acetic acid.

Methods of Use

As discussed above, the antimicrobial compositions of the present invention are useful in the cleaning and reduction of microbial population of various surfaces found in food sanitizing, food processing, food services and the health care industry as well as in water treatment. Surfaces could include: the surface of a vegetable or fruit, floors, counters, furniture, architectural surfaces, porous surfaces (e.g., textiles, wall paper, carpeting, etc.), medical tools and equipment, food service wares, skin, animal enclosures, feeding stations, veterinarian surgical or examination areas, etc.

Preferably, the antimicrobial compositions of the present invention possess several properties in addition to antimicrobial efficacy. The compositions are preferably no rinse after application, and have residual antimicrobial activity. Residual activity implies a film of sanitizing material which will continue to have antimicrobial effect if the treated surface is contaminated by microorganisms during a period after application of the composition. Additionally, in some instances, the compositions are odor free to prevent transfer of undesirable odors onto foodstuff.

The actual cleaning of the target surface can be optionally accomplished with a different material than the compositions of the present invention. A formulated detergent can be introduced with water. After the cleaning step, a composition disclosed herein can be applied or introduced into the system. The present antimicrobial solution is typically found to remain in solution in a range of solution temperatures (e.g., 0–100° C.).

A method of reducing microbial population of surfaces comprises the following steps. The use composition of the invention is introduced onto the surface at a temperature in the range of about 0 to 100° C. After introduction of the use solution, the solution is allowed to remain on the surface for a time sufficient to be effective in reducing the microbial population of the surface (i.e., to kill undesirable microbes). After sufficient time for microbial reduction, the use solution is removed.

A method of treating substantially fixed in-place process facilities comprises the following steps. The use composition of the invention is introduced into the process facilities at a temperature in the rage of about 0 to 100° C. After introduction of the use solution or concentrate, the solution is circulated throughout the system for a time sufficient for reduction in microbial population in the process facility. After the system has been treated with the use solution, it is drained from the system. Upon completion of the treatment, the system optionally may be rinsed with water or other such material. The composition can be circulated through the process facility for a period of time which can be varied according to treatment conditions, for example it may be 15 minutes or less.

The composition may also be employed by dipping food processing equipment into the solution, soaking the equipment for a time sufficient to reduce the microbial population from the equipment, or spraying or wiping the food processing equipment. In general, the composition should stay in contact with the equipment for a time sufficient to reduce the microbial population of the surfaces. Excess solution is removed by wiping, vertically draining, vacuuming, etc. Suitable soaking times are generally under 10 minutes but may range up to an hour or more depending on the concentration of the peroxygen compound, amine oxide or other components of the composition as discussed herein.

The composition of the present invention may also be employed for reducing the microbial population of clothing items or fabrics. A dilute or concentrate composition can be injected into the wash or rinse water of a laundry machine and contacted with contaminated fabric for a time sufficient to sanitize the fabric. As above, suitable times are generally under 10 minutes but may range up to an hour or more depending on the concentration of the peroxygen compound, amine oxide or other components of the composition as discussed herein. Excess solution can then be removed by rinsing with water or other such material or centrifuging the fabric.

EXAMPLES

The following Examples are intended to illustrate the above invention and should not be construed so as to narrow its scope.

Example 1

An experiment was conducted to determine the Minimal Bactericidal Concentration (MBC) of octyldimethylamine oxide alone, hydrogen peroxide alone and two mixtures of octyldimethylamine oxide with hydrogen peroxide against *Pseudomonas aeruginosa*. Experiments were conducted using standard bacteriological techniques, specifically Ecolab Microbiological Services S.O.P. Method MS009 (reference to A.O.A.C. Method 960.09). As shown in Table I, when used alone the concentration of octyldimethylamine oxide required to obtain MBC was greater than 2000 parts per million. A similar result was obtained when hydrogen peroxide was administered alone. However, at a weight ratio of 1.0:1.5–1:1 amine oxide:hydrogen peroxide the concentration required of octyldimethylamine oxide and hydrogen peroxide to obtain MBC was 850 parts per million. The 50%/50% relative composition of amine oxide:hydrogen peroxide has a pH of 7.4 and an oxidation potential of 250 mV when diluted to 1.7% total oxidizer.

TABLE I

Comparison of Antimicrobial Activity

| Relative % Composition | | MBC | |
| --- | --- | --- | --- |
| Amine Oxide | Hydrogen Peroxide | ppm peroxide | ppm amine oxide |
| 0 | 100 | >2,000 | 0 |
| 25 | 75 | 850 | 212 |
| 50 | 50 | 850 | 850 |
| 100 | 0 | 0 | >2,000 |

Example 2

A second composition of the present invention was prepared as described in Example 1, except peracetic acid and acetic acid were added to the blend. The mixture was prepared containing 16.8% octyldimethylamine oxide, 16.0% hydrogen peroxide, 21.9% peracetic acid and 45.4% acetic acid. Dilution of the mixture gave a pH of 4.0 and an oxidation potential of 550 mV when diluted to 1.7% total oxidizer concentration.

Example 3

A second experiment was conducted to determine the synergistic effects of mixing an amine oxide, peracetic acid and hydrogen peroxide. Combinations of peracetic acid and hydrogen peroxide were measured in the presence and absence of a tetradecyl-dimethylamine oxide for antimicrobial activity against *Salmonella javiana*. Testing was performed on a tomato surface. As shown in Table II, when used alone, the peracetic acid and hydrogen peroxide were fairly ineffective at reducing the numbers of *S. javiana*. Additionally, when the tetradecyl-dimethylamine oxide was used alone it too was fairly ineffective at reducing or antimicrobial activity against *S. javiana*. However, at a ratio of 3.5:1.0 of tetradecyl-dimethylamine oxide:peracetic acid+hydrogen peroxide mixture) the antimicrobial activity of the composition marketly improved. To demonstrate that the effect of the antimicrobial activity was not the result of reduced surface tension, a similar ratio (3.5:1.0) of Pluronic F108 (nonionic surfactant) to peracetic acid/hydrogen peroxide was combined and applied against *S. javiana*. The result demonstrated that mere surface tension reduction by a nonionic surfactant, in combination with the peroxygen activity, does not substantially improve the microbial kill of the peroxygen compound alone.

TABLE II

Synergistic Ratio of an Amine Oxide:Hydrogen Peroxide/Peracetic Acid Mix

| Composition | Amine Oxide (ppm) | Hydrogen Peroxide (ppm) | Peracetic Acid (ppm) | Nonionic Surfactant (ppm) | Log Reduction (S. Javiana) |
|---|---|---|---|---|---|
| Amine Oxide Alone | 425 | 0 | 0 | 0 | <0.2 |
| Peroxygen Alone | 0 | 58 | 80 | 0 | <0.2 |
| Nonionic Surfactant/ Peroxygen | 0 | 58 | 80 | 500 | <0.6 |
| Amine Oxide/ Peroxygen | 425 | 58 | 80 | 0 | >5.0 |

From the foregoing detailed description and examples, it will be evident that modifications and variations can be made in the products and processes of the invention without departing from the spirit and scope of the invention. Therefore, it is intended that all modifications and variations not departing from the spirit of the invention come within the scope of the claims and their equivalents.

We claim:

1. An antimicrobial composition comprising:
   hydrogen peroxide; and
   amine oxide of the formula $(R_1R_2R_3)NO$, wherein $R_1$ is an octyl group and $R_2$ and $R_3$ are alkyl groups having 1 to 2 carbon atoms;
   wherein the amine oxide and hydrogen peroxide are present at a weight ratio of 1:3 to 3:1;
   the composition having a minimum bactericidal concentration of less than 2000 ppm of hydrogen peroxide, amine oxide, or a combination thereof.

2. The composition of claim 1, comprising octyldimethylamine oxide.

3. The composition of claim 1, comprising 10 to 10,000 ppm hydrogen peroxide and 10 to 10,000 ppm of amine oxide.

4. The composition of claim 1, comprising 500 to 2,000 ppm hydrogen peroxide and 500 to 2,000 ppm of amine oxide.

5. The composition of claim 1, comprising 0.1 to 40 wt-% hydrogen peroxide and 0.1 to 40 wt-% of amine oxide.

6. The composition of claim 1, wherein hydrogen peroxide is the only peroxygen compound in the composition.

7. The composition of claim 1, wherein the composition is free of nonionic surfactant.

8. The composition of claim 1, consisting essentially of hydrogen peroxide and amine oxide.

9. The composition of claim 8, wherein the composition is free of nonionic surfactant.

10. A method for reducing microbial population on contaminated surfaces comprising:
    selecting an antimicrobial composition comprising:
       hydrogen peroxide; and
       amine oxide of the formula $(R_1R_2R_3)NO$, wherein $R_1$ is an octyl group and $R_2$ and $R_3$ are alkyl groups having 1 to 2 carbon atoms;
       wherein the amine oxide and hydrogen peroxide are present at a weight ratio of 1:3 to 3:1;
       the composition having a minimum bactericidal concentration of less than 2000 ppm of hydrogen peroxide, amine oxide, or a combination thereof; and
    contacting the contaminated surface with the antimicrobial composition.

11. The process of claim 10, wherein the contaminated surface is an inanimate solid surface contaminated by a microbial population selected from the group consisting of bacteria, protozoa, fungi, viruses, spores, and mixtures thereof.

12. The process of claim 10, wherein the contaminated surface is an inanimate porous surface contaminated by a microbial population selected from the group consisting of bacteria, protozoa, fungi, viruses, spores, and mixtures thereof.

13. The process of claim 10, wherein the contaminated surface comprises the surface of food service equipment.

14. The process of claim 10, wherein the contaminated surface comprises the surface of a fabric.

15. The process of claim 10, wherein the contaminated surface is an architectural surface.

16. A method of reducing the microbial population of substantially fixed in-place process facilities comprising the steps of:
    introducing into the process facility a composition comprising:
       hydrogen peroxide; and
       amine oxide of the formula $(R_1R_2R_3)NO$, wherein $R_1$ is an octyl group and $R_2$ and $R_3$ are alkyl groups having 1 to 2 carbon atoms;
       wherein the amine oxide and hydrogen peroxide are present at a weight ratio of 1:3 to 3:1;
       the composition having a minimum bactericidal concentration of less than 2000 ppm of hydrogen peroxide, amine oxide, or a combination thereof;
    circulating the composition through the process facilities for a time sufficient to reduce the microbial population of the process facilities; and
    draining the composition from the process facility.

* * * * *

UNITED STATES PATENT AND TRADEMARK OFFICE
CERTIFICATE OF CORRECTION

PATENT NO.      : 6,479,454 B1
DATED           : November 12, 2002
INVENTOR(S)     : Smith et al.

It is certified that error appears in the above-identified patent and that said Letters Patent is hereby corrected as shown below:

<u>Title page,</u>
Item [56], References Cited, U.S. PATENT DOCUMENTS, "4,244,844" should read -- 4,244,884 --.

Signed and Sealed this

Twenty-fourth Day of June, 2003

JAMES E. ROGAN
*Director of the United States Patent and Trademark Office*